(12) United States Patent
Koziol

(10) Patent No.: US 7,008,447 B2
(45) Date of Patent: Mar. 7, 2006

(54) METHOD FOR PRODUCING A MULTIFOCAL CORNEAL SURFACE USING INTRACORNEAL MICROSCOPIC LENSES

(76) Inventor: Jeffrey E. Koziol, 14 Ambrose, South Barrington, IL (US) 60010

(*) Notice: Subject to any disclaimer, the term of this patent is extended or adjusted under 35 U.S.C. 154(b) by 0 days.

(21) Appl. No.: 10/608,545

(22) Filed: Jun. 30, 2003

(65) Prior Publication Data

US 2004/0078075 A1   Apr. 22, 2004

Related U.S. Application Data

(63) Continuation of application No. 09/852,846, filed on May 11, 2001, now Pat. No. 6,589,280.

(51) Int. Cl.
*A61F 2/14* (2006.01)

(52) U.S. Cl. .................. 623/5.11; 623/5.13; 623/6.28; 623/6.34

(58) Field of Classification Search .................. 606/65; 623/5.11, 5.12, 5.15, 6.24, 6.27, 6.28, 6.3, 623/6.32, 6.34, 5.13, 5.14
See application file for complete search history.

(56) References Cited

U.S. PATENT DOCUMENTS

| | | | |
|---|---|---|---|
| 4,704,016 A | 11/1987 | de Carle | |
| 4,840,175 A | 6/1989 | Peyman | |
| 4,906,245 A | 3/1990 | Grendahl | |
| 5,024,517 A | 6/1991 | Seidner | |
| 5,196,026 A | 3/1993 | Barrett et al. | |
| 5,722,971 A | 3/1998 | Peyman | |
| 5,806,530 A | 9/1998 | Herrick | |
| 5,919,185 A | 7/1999 | Peyman | |
| 5,964,748 A | 10/1999 | Peyman | |
| 6,015,435 A | 1/2000 | Valunin et al. | |
| 6,059,775 A | 5/2000 | Nielsen | |
| 6,063,073 A | 5/2000 | Peyman | |
| 6,086,204 A | 7/2000 | Magnante | |
| 6,090,141 A | 7/2000 | Lindstrom | |
| 6,102,946 A * | 8/2000 | Nigam | ...................... 623/5.15 |
| 6,228,113 B1 | 5/2001 | Kaufman | |
| 6,277,146 B1 | 8/2001 | Peyman et al. | |
| 6,589,280 B1 | 7/2003 | Koziol | |
| 6,702,807 B1 * | 3/2004 | Peyman | ........................ 606/5 |

* cited by examiner

*Primary Examiner*—David H. Willse
*Assistant Examiner*—Javier G. Blanco
(74) *Attorney, Agent, or Firm*—Roylance, Abrams, Berdo & Goodman, L.L.P.

(57) ABSTRACT

A method for correcting vision of an eye, including the steps of separating a portion of the cornea to form first and second internal surfaces in the cornea, and then placing at least one microscopic lens in between the first and second internal surfaces in the cornea, so that the external surface of the cornea is not substantially displaced. In a preferred embodiment, the microscopic lenses can be placed in concentric circles around the main optical axis so that the lenses form multifocal or bifocal vision.

10 Claims, 4 Drawing Sheets

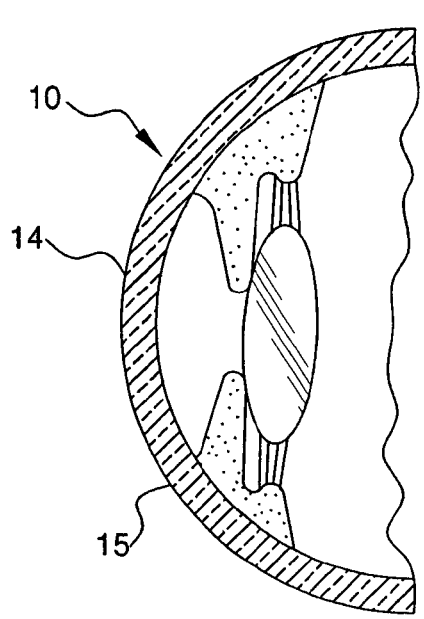
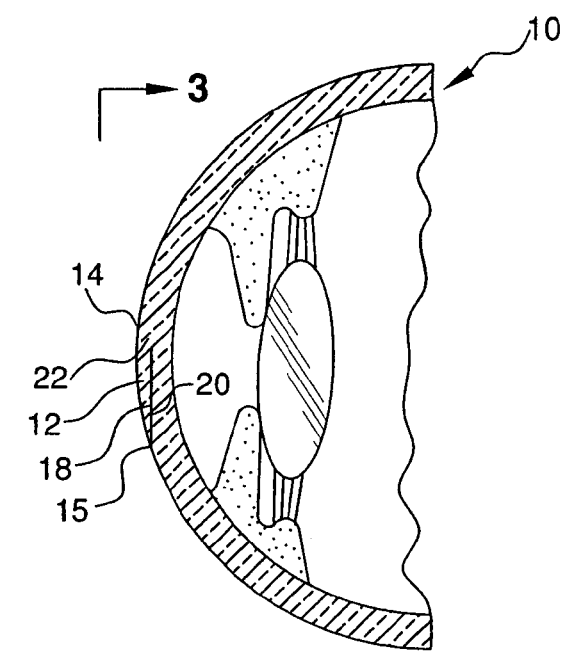
FIG. 1      FIG. 2
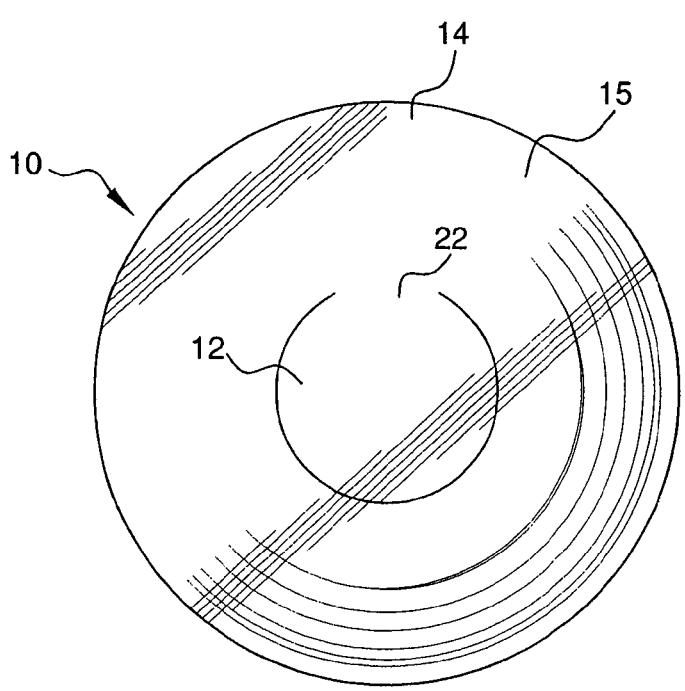
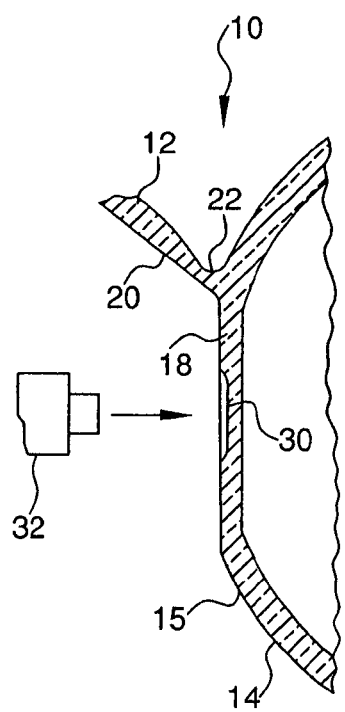
FIG. 3      FIG. 4

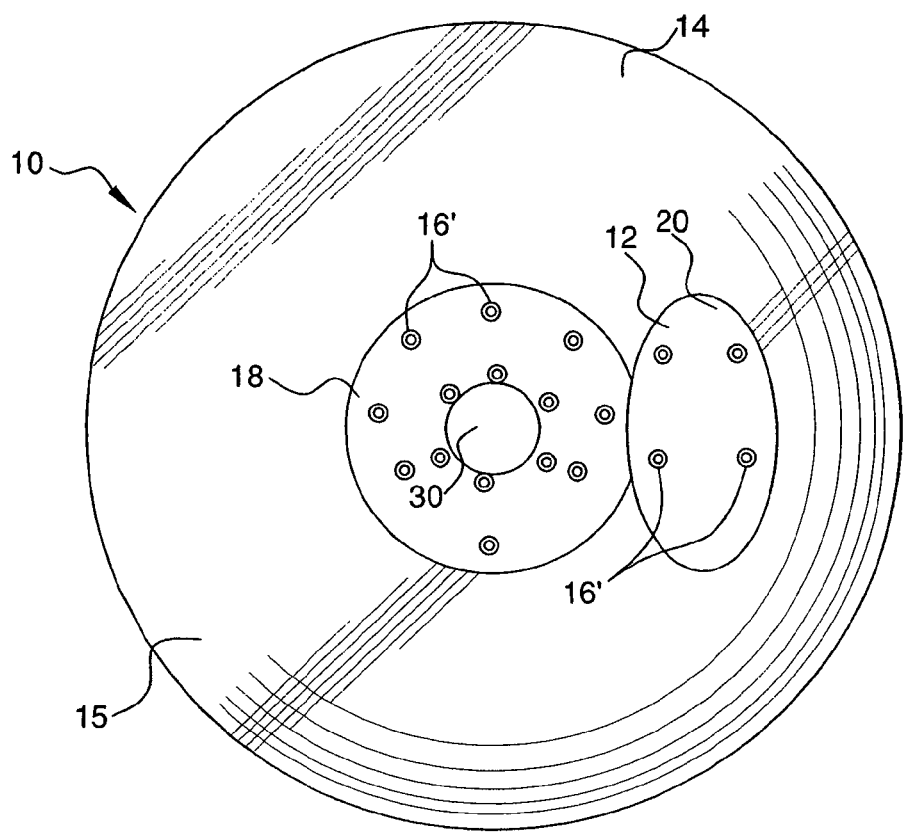
FIG. 8
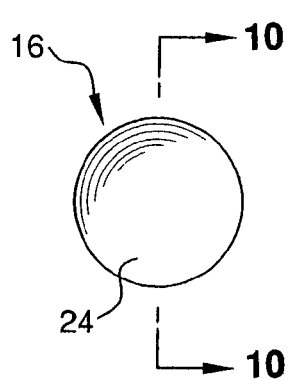 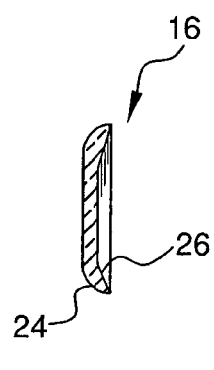 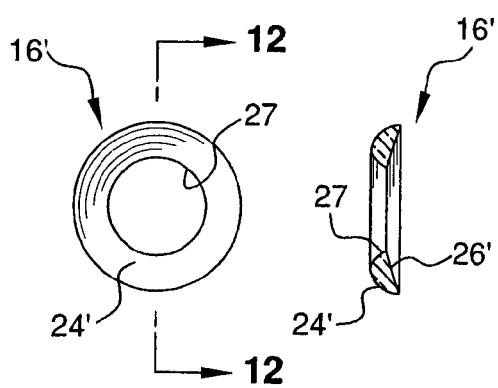
FIG. 9   FIG. 10   FIG. 11   FIG. 12

METHOD FOR PRODUCING A MULTIFOCAL CORNEAL SURFACE USING INTRACORNEAL MICROSCOPIC LENSES

CROSS-REFERENCE TO RELATED APPLICATION

This application is a continuation application of Ser. No. 09/852,846, filed May 11, 2001, now U.S. Pat. No. 6,589,280, issued Jul. 8, 2003, the entire contents of which are herein incorporated by reference.

FIELD OF THE INVENTION

The present invention relates to implanting microscopic lenses in a live cornea of an eye to help correct the vision in the eye by producing a multifocal corneal surface. More particularly, the present invention relates to inserting microscopic lenses under a corneal flap after a surgical procedure, such as LASIK eye surgery, to correct the vision in the eye by producing a multifocal corneal surface without substantially displacing the external corneal surface.

BACKGROUND OF THE INVENTION

Conventional surgical techniques use ultraviolet light and short wavelength lasers to modify the shape of the cornea. For example, excimer lasers, such as those described in U.S. Pat. No. 4,840,175 to Peyman, which is incorporated herein by reference, emit pulsed ultraviolet radiation, which can be used to decompose or photoablate tissue in the live cornea to reshape the cornea.

Specifically, the Peyman patent discloses the laser surgical technique known as laser in situ keratomycosis (LASIK). In this technique, a portion of the front of the live cornea can be cut away in the form of a flap having a thickness of about 160 microns. This cut portion is moved away from the live cornea to expose an inner surface of the cornea. A laser beam is then directed onto the exposed inner surface to ablate a desired amount of the inner surface up to 150–180 microns deep. The cut portion is reattached over the ablated portion of the cornea and assumes a shape conforming to that of the ablated portion. The LASIK procedure is generally sufficient to correct myopia or distance vision. However, in many patients while the LASIK procedure is sufficient to correct distance vision it does not correct reading vision in patients who are presbyopic. Presbyopia is a condition which occurs after age 40 in which the lens of the eye loses its ability to change focus. When a distinctive object is in sharp focus on the retina, close objects are out of focus or blurred. To bring close objects into focus the lens of the eye changes shape to bring these objects into focus. This rapid movement of the lens occurs without conscience thought through and allows objects to be brought into focus. When the lens of the eye losses this ability, reading glasses or bifocal glasses are used. When a patient in their 40's and 50's have laser surgery and achieve corrected distance vision they still need glasses for reading. There are frequently 2 pairs needed one for intermediate distance, such as the computer and one for close reading vision.

Additional methods for correcting the refractive error in the eye include inserting an implant in between layers of the cornea. Generally, this is achieved using several different methods. The first method involves inserting a ring between layers of the cornea, as described in U.S. Pat. No. 5,405,384 to Silvestrini. Typically, a dissector is inserted in to the cornea to form a channel therein. Once the dissector is removed, a ring is then inserted into the channel to alter the curvature of the cornea. In the second method, a flap can be created similarly to the LASIK procedure, described above, and a large lens can be inserted under the flap to change the shape of the cornea, as described in U.S. Pat. No. 5,919,785 to Peyman and U.S. Pat. No. 6,102,946 to Nigam. The third method involves forming a pocket using a mechanical instrument, and inserting an implant into the pocket, as described in U.S. Pat. No. 4,655,774 to Choyce. These procedures all induce a single corneal curvature change and do not correct both distance vision and close vision in a bifocal or multifocal manner.

Additionally, even though these existing intracorneal lenses are somewhat suitable for correcting distant vision disorders, they typically cause the eye to experience an undesirable side effect commonly referred to as a "halo effect", which is a ring of light that a person will see in the eye having an implanted intracorneal lens. A halo effect is caused due to light entering into or being refracted by the intracorneal lens at certain angles which creates a glare that is sensed by the retina of the eye and thus experienced by the person.

Although the severity of the halo effect can vary depending on the shape of the intracorneal lens and the amount of direct and ambient light being received by the eye, the halo effect can cause the patient much annoyance. Also, in certain instances, the halo effect can also adversely affect the patient's ability to read, drive a car and perform other routine activities requiring acute vision.

Additionally, many of these conventional techniques require relatively large lenses or corneal implants that stretch or expand the corneal surface to accommodate the intracorneal lens. These large lenses can lead to corneal erosion, which is generally caused by corneal cells dying since the lens does not allow nutrients to flow through portions of the cornea.

Accordingly, a need exists for intracorneal lenses, which can help correct the vision in the eye without displacing the corneal surface, while simultaneously eliminating or reducing glare and the halo effect due to light reflecting off of the intracorneal lens.

SUMMARY OF THE INVENTION

Accordingly, it is an object of the present invention is to provide an improved method for correcting the vision of an eye.

Another object of the present invention is to provide a method for correcting the vision of an eye by inserting or implanting an intracorneal lens.

Still another object of the present invention is to provide a method for correcting the vision of an eye by inserting an intracorneal lens, without the lens substantially altering the shape of the cornea, so that undue tension is not experienced by the corneal flap.

Yet another object of the present invention is to provide a method for correcting the vision of an eye by inserting an intracorneal lens that changes the refraction of the eye by having a different refractive index than the corneal tissue.

Yet another object of the present invention is to provide a method for correcting the vision of an eye using multiple microscopic lenses, so that glare can be reduced or eliminated.

Yet another object of the present invention is to provide a method for correcting the vision of an eye by placing multiple microscopic lenses under a corneal flap.

Yet another object of the present invention is to provide a method for correcting the distance vision and close vision of an eye.

The foregoing objects are basically attained by a method for correcting vision of an eye, the eye having a cornea with an external surface and an optical axis, comprising the steps of separating a portion of the cornea to form first and second internal surfaces, and placing at least one microscopic lens in between the first and second internal surfaces, so that the external surface of the cornea is not substantially displaced.

Other objects, advantages, and salient features of the present invention will become apparent to those skilled in the art from the following detailed description, which, taken in conjunction with the annexed drawings, discloses preferred embodiments of the invention.

BRIEF DESCRIPTION OF THE DRAWINGS

Referring to the drawings which form a part of this disclosure:

FIG. 1 is a cross-sectional side view of an eye.

FIG. 2 is a cross-sectional side view of the eye of FIG. 1 with a flap formed thereon.

FIG. 3 is a front elevational view taken along lines 3—3 of FIG. 2.

FIG. 4 is a cross-sectional side view of the eye in FIG. 3 with the flap moved away from the surface of the cornea and a laser ablating an exposed surface of the cornea.

FIG. 8 is a front elevational view of an eye undergoing the preferred method of the present invention, wherein the microscopic lenses are substantially ring-shaped.

FIG. 9 is a front elevational view of a microscopic lens used in the method described herein.

FIG. 10 is a cross-sectional side view taken along lines 10—10 of FIG. 9.

FIG. 11 is a front elevational view of a substantially ring-shaped microscopic lens used in the method described herein.

FIG. 12 is a cross-sectional side view taken along lines 12—12 of FIG. 11.

DETAILED DESCRIPTION OF THE PREFERRED EMBODIMENT

Figure 5:
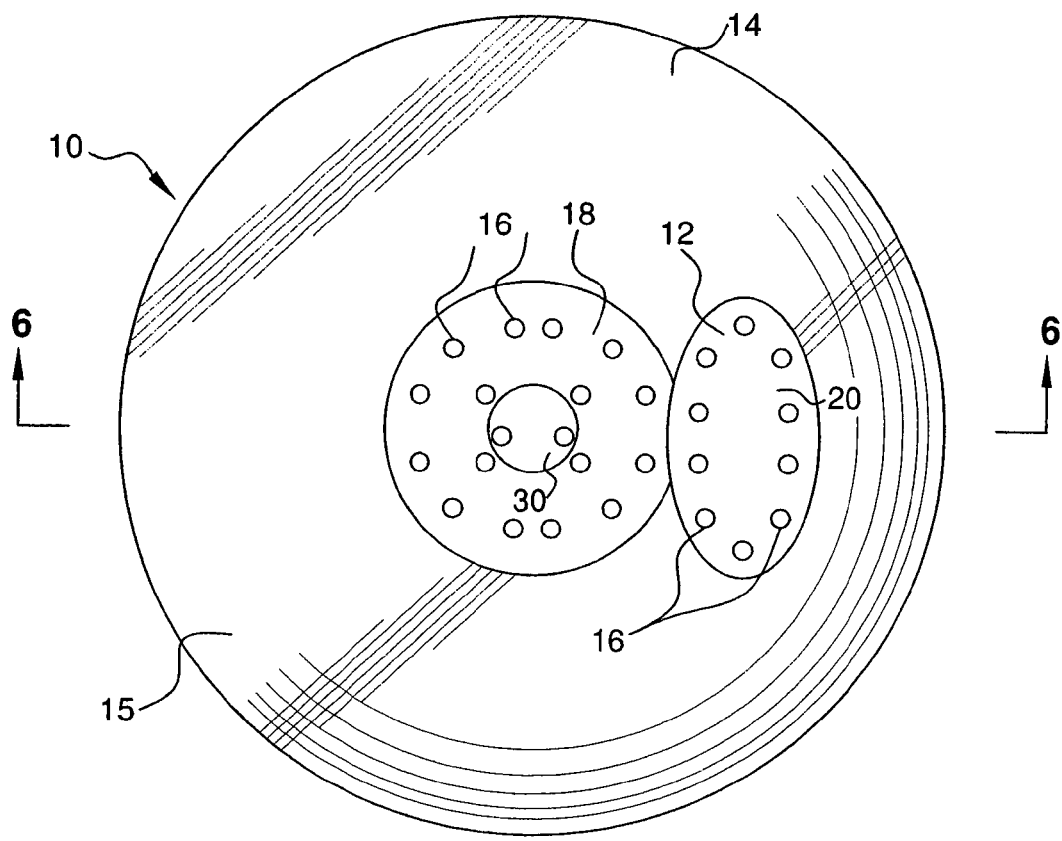
FIG. 5 is a front elevational view of an eye undergoing a preferred method of the present invention, specifically, microscopic lenses are placed on both the first and second exposed internal corneal surfaces.

As seen in FIGS. 1–7, the refractive properties of eye 10 can be altered by creating a corneal flap 12 in the cornea 14, ablating the cornea to reshape the cornea and the external surface 15 of the cornea, and then placing multiple microscopic lenses or inlays 16 under flap 12.

To begin, the refractive error in the eye is measured using wavefront technology, or any other measurement device desired, as is known to one of ordinary skill in the art. For a more complete description of wavefront technology see U.S. Pat. No. 6,086,204 to Magnate, the entire contents of which is incorporated herein by reference. The refractive error measurements are then used to determine the proper correction necessary. For example, the information from the wavefront technology determines the proper portions of the cornea of the eye to be ablated, if necessary, and the proper power of the lenses 16 and/or the number of the lenses 16 to be implanted.

As seen in FIGS. 2 and 3, flap 12 is created on the surface of the cornea by using a tool or device (not shown) that is known to one skilled in the art, such as a microkeratome. The device separates the cornea and exposes a first surface 18 and a second surface 20. The first surface 18 faces in an anterior direction and the second surface 20 faces in a posterior direction of the eye. The flap is moved to expose second surface 20 using a spatula, forceps or any other device desired. The flap 12 is preferably coupled or connected to the cornea by a portion 22 that allows the flap to be moved away from or pealed from surface 18 in a hinged manner, as seen specifically in FIGS. 4–6 and 8. However, the flap does not necessarily need to be coupled to the cornea in a hinged manner and can be fully removed from the cornea or a pocket can be formed underneath the external surface of the cornea, with an incision allowing access to the pocket.

If the refractive error of the cornea requires correcting for distance vision, such as myopia, the LASIK procedure or any other technique known in the art can be preformed. Preferably, LASIK, as disclosed in U.S. Pat. No. 4,840,175 to Peyman and is known to one of ordinary skill in the art, is used and preferably a portion 30 of surface 18 and surface 20 of the cornea under corneal flap 12 is ablated using an excimer laser 32 to achieve the proper corrective vision for distances, as seen in FIG. 4. However, a portion of surface 20 can be ablated or a portion of both surfaces 18 and 20 can be ablated. If no distance vision correction is required, it is not necessary to perform the LASIK procedure or any other distance corrective procedure known in the art.

Figure 13:
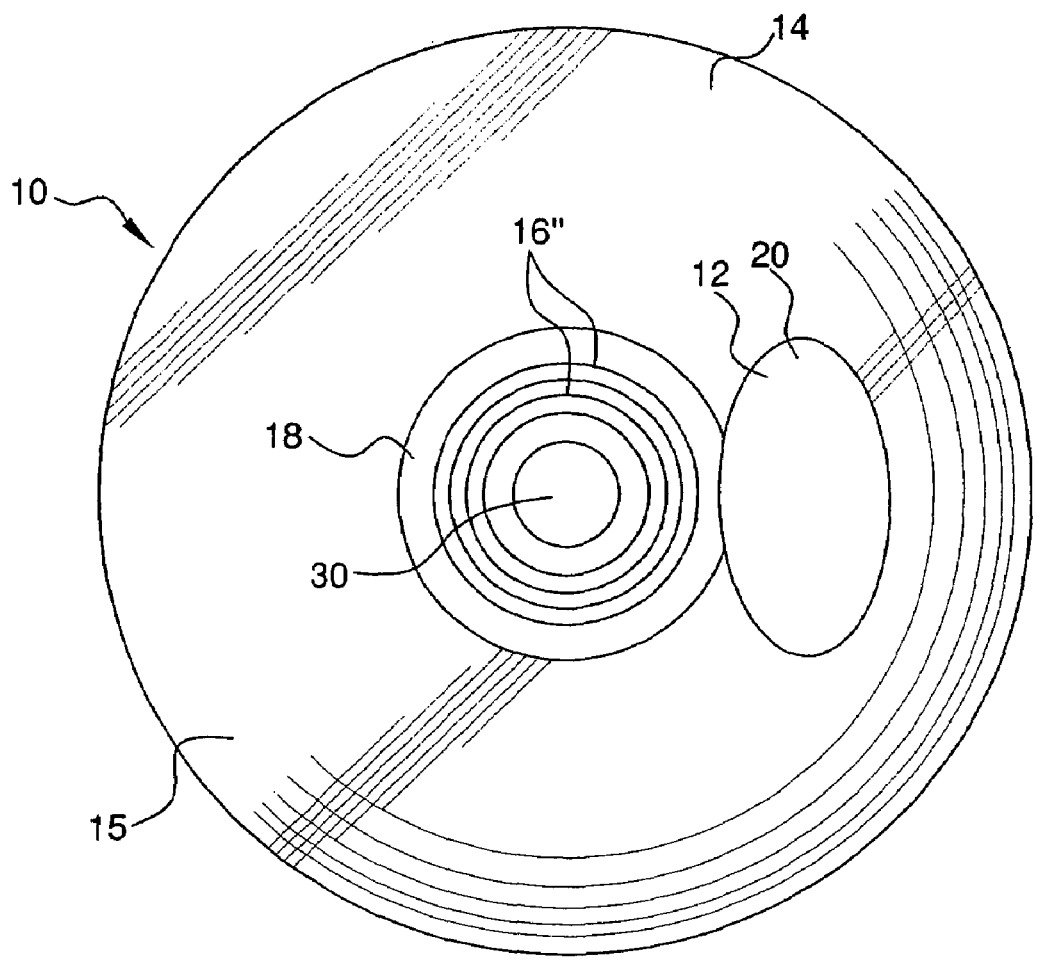
FIG. 13 is a front elevational view of an eye undergoing the preferred method of the present invention, wherein there is one substantially ring-shaped lens having a microscopic ring portion.
Figure 14:
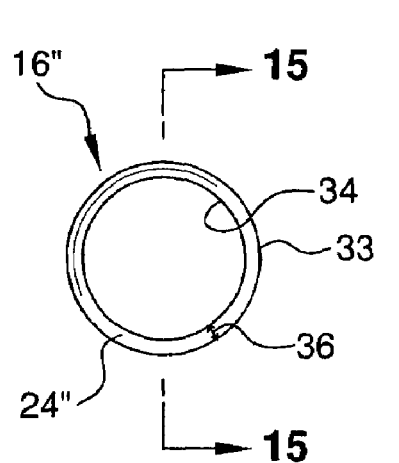
FIG. 14 is a front elevational view of a substantially ring-shaped lens having a microscopic ring portion used in the method described herein.
Figure 15:
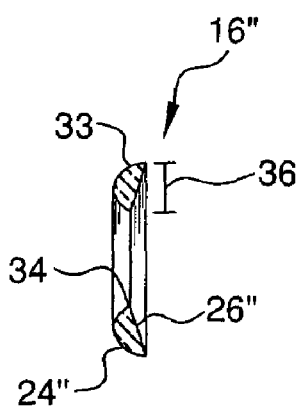
FIG. 15 is a cross-sectional side view taken along lines 15—15 of FIG. 14.

Furthermore, as shown in FIG. 13, microscopic lens 16" can be a substantially ring shaped lens with an arcuate cross section and first and second surfaces 24" and 26", as seen in FIGS. 14 and 15. Lens 16" has an outside wall or surface 33 and inside wall or surface 34 that have diameters that are sufficiently large enough to encircle the main optical axis of the eye 28 with the center of the ring, aligned with the main optical axis. In other words, the diameter of wall 32 is preferably about 3–5 millimeters, but can be any size desired. However, the distance or ring portion 36 between wall 33 and wall 34 and the thickness of lens 16" is preferably microscopic. As described above, microscopic as defined herein means preferably that distance 36 is about 1 millimeter and the thickness of lens 16" is about 1–50 microns thick, and more preferably, distance 36 is less than about 1 millimeter and lens 16" is about 2–3 microns thick. Preferably, multiple rings 16" are placed under the flap, as shown in FIG. 13. The lenses are placed or positioned in concentric circles of about 3, 4 and/or 5 millimeters around the main optical axis, each having a different refractive power, thus allowing multifocal vision. However, any number of lenses can be placed around the main optical axis and, including only one or any number greater than one, and the lenses may each have the same refractive power or any combination of the same or different refractive power. In other words, two lenses can have the same refractive power and one lens can have a different refractive power.

Furthermore, as shown in FIG. 13, microscopic lens 16" can be a substantially ring shaped lens with an arcuate cross section and first and second surfaces 24" and 26", as seen in FIGS. 14 and 15. Lens 16" has an outside wall or surface 32 and inside wall or surface 34 that have diameters that are sufficiently large enough to encircle the main optical axis of the eye 28 with the center of the ring, aligned with the main optical axis. In other words, the diameter of wall 32 is preferably about 3–5 millimeters, but can be any size desired. However, the distance or ring portion 36 between wall 32 and wall 34 and the thickness of lens 16" is preferably microscopic. As described above, microscopic as defined herein means preferably that distance 36 is about one millimeter and the thickness of lens 16" is about 1–50 microns thick, and more preferably, distance 36 is less than about one millimeter and lens 16" is about 2–3 microns thick. Preferably, multiple rings 16" are placed under the flap, as shown in FIG. 13. The lenses are placed or positioned in concentric circles of about 3, 4 and/or 5 millimeters around the main optical axis, each having a different refractive power, thus allowing multifocal vision. However, any number of lenses can be placed around the main optical axis and, including only one or any number greater than one, and the lenses may each have the same refractive power or any combination of the same or different refractive power. In other words, two lenses can have the same refractive power and one lens can have a different refractive power.

Lenses 16, 16' and 16" are preferably formed of any polymer or synthetic material desired, such as plastic, glass, silicon, methametacolade, or any acrylic that preferably has a refractive index that is different from the refractive index of the cornea. However, the lenses may be any material desired that would help correct the refractive error in the cornea.

Preferably, second surface 26 of at least one microscopic lens 16 is placed on the first corneal surface 18 of cornea 14. However, first surface 24 may be placed on second corneal surface 20 or any combination thereof when multiple lenses are used. For example, first surface 24 of at least one lens can be placed on corneal surface 20, while second surface 26 of at least one lens can be placed on corneal surface 18.

More preferably, when lenses 16 and 16' are used, about 50 microscopic lenses are placed in between the first and second surfaces 18 and 20; however, any number of lenses desired to correct the refractive error in the cornea can be placed in between the first and second surfaces 18 and 20. Depending on the power of the lenses, by inserting the lenses in this manner an eye will be able to see with either bifocal or multifocal vision. For example, about 50 lenses, each having the same power can be placed in concentric circles about the main optical axis 28 of the eye. This pattern would allow the patient to view distance vision using the portion of the eye that has no microscopic lenses, while the portions that had microscopic lenses would allow a patient to view objects close, such as for the purpose of reading. Additionally, different power lenses can be implanted that would allow multifocal vision. For example, one array of about 20 plus 1.5 diopter lenses can be placed in the eye in any manner desired (i.e. a concentric circle), while a second array of about 20 plus 2 diopter lenses can also be placed in the eye in any manner desired (i.e. a concentric circle). Furthermore, when using lens 16", multiple lenses can be used in concentric circles, each lens having either the same refractive index as each other lens, or a different refractive index or any combination thereof that would allow bifocal or multifocal vision as described above. This allows several different focusing points for the eye, allowing the patient to see a variety of near and far distances.

Figures 6, 7:
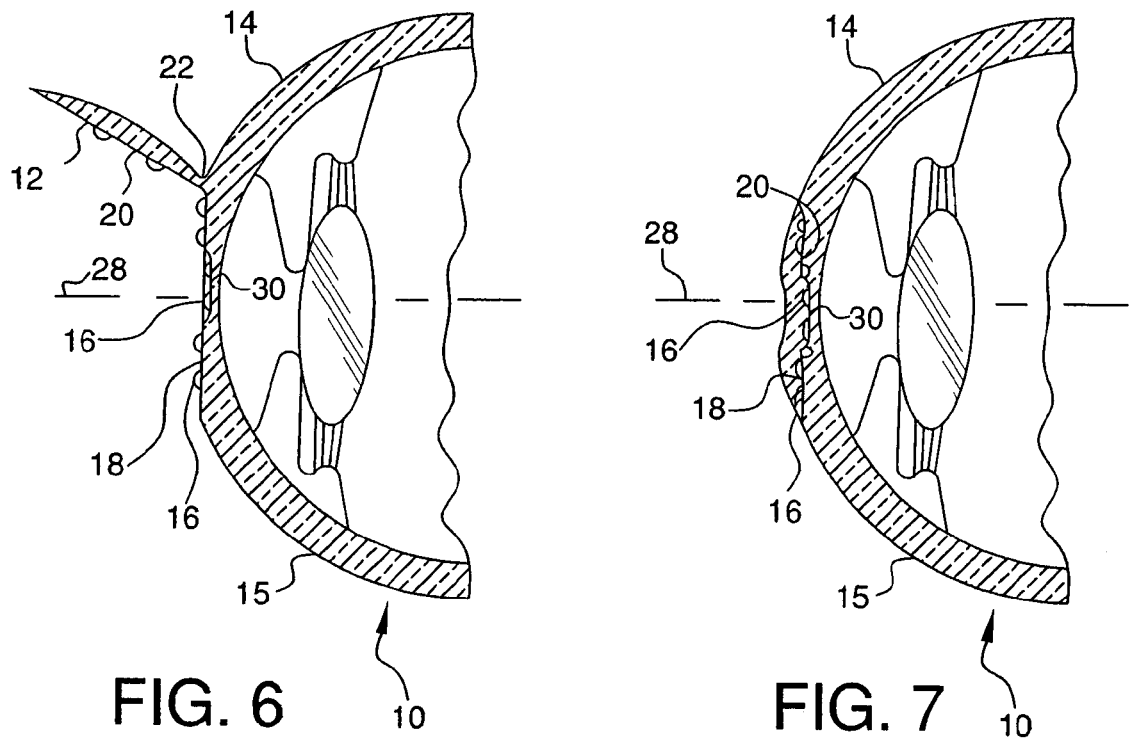
FIG. 6 is a cross-sectional side view taken along lines 6—6 of FIG. 5.
FIG. 7 is a cross-sectional side view of the eye of FIG. 6 with the flap replaced over the exposed surface of the cornea and the microscopic lenses.

As seen in FIG. 7, once the lens or lenses are in place, the flap is replaced or repositioned on the cornea. Preferably, surface 20 is placed back over surface 18, in the same position prior to removing flap 12. The flap is then sutured or reattached to the cornea in any manner desired or simply replaced and allowed to heal.

Since each of the lenses 16 are preferably less than about 2–3 microns thick, the first corneal surface 18 is not substantially displaced away from second corneal surface 20. In other words, the exterior surface of the cornea has approximately the same curvature as the eye originally has or has after the distance correcting procedure. This allows little or no tension to be exerted over the flap 12 when it is reattached and allows for a relatively precise fit of surface 18 and surface 20.

Additionally, the lenses 16 allow for bifocal and multifocal vision by focusing the light passing therethrough on a different portion of the retina, since the refractive power of each lens is different from the refractive power of the cornea. Therefore, once it is known what refractive error is in the cornea and the eye, the only values to be determined are whether distance correction is necessary, the power of the lenses, or the powers of the lenses for multifocal purposes, and the number of lenses.

The implantation of microscopic lenses 16 allow vision correction, while being small enough so as to not produce significant glare refracted from the lenses or substantially displace the surface of the cornea or the flap 12. This procedure improves vision without discomforting glare problems or the undue stress on the cornea experienced by the prior art.

Any discussion of lens 16 and sides 24 and 26 applies to lenses 16' and 16" and to sides 24', 24", 26' and 26".

While preferred embodiments have been chosen to illustrate the invention, it will be understood by those skilled in the art that various changes and modifications can be made therein without departing from the scope of the invention as defined in the appended claims.

What is claimed is:

1. A method for correcting vision in an eye, the eye having a cornea with an external surface and an optical axis, comprising the steps of
    separating a portion of the cornea to form first and second internal surfaces,
    placing a first lens having a first opening therein between the first and second internal surfaces, the first opening being substantially centered about the optical axis, the first lens having a first inner wall defined by the first opening, a first outer wall, and a thickness between about one and about 50 microns, and
    placing a second lens having a second opening therein between the first and second internal surfaces, the second opening being substantially centered about the optical axis and concentric with the first lens, the second lens having a second inner wall defined by the second opening, a second outer wall and a thickness between about one and about 50 microns.

2. A method according to claim 1, wherein
    the placing step includes placing at least one of the first and second lenses substantially concentrically about the optical axis of the eye.

3. A method according to claim 1, wherein the placing step includes placing both the first and second lenses substantially concentrically about the optical axis of the eye.

4. A method according to claim 1, wherein the first and second lenses have a thickness of about 2–3 microns, so that when the first and second lenses are inserted between the first and second internal surfaces, the first and second internal surfaces are not substantially displaced.

5. A method according to claim 4, wherein the separating step includes separating the portion of the cornea to form a corneal flap.

6. A method according to claim 5, further including the steps of
moving the corneal flap to expose the first and second internal surfaces, and
replacing the corneal flap after the first and second lenses have been placed in between the first and second internal surfaces.

7. A method according to claim 6, wherein the first and second lenses each have a power of about plus one to about plus three diopters.

8. An intracorneal lens system for implantation in the eye to correct refractive error thereof, comprising:
a first lens portion having a first outer surface and a thickness of between about one and about 50 microns, said first outer surface defining a first outer diameter;
a first aperture extending through said first lens portion, said first aperture defining a first inner diameter and a first inner surface;
a second lens portion having a second outer surface and a thickness of between about one and about 50 microns, the second outer surface defining a second outer diameter, the second lens portion being substantially concentric to the first lens portion; and
a second aperture extending through said second lens portion, said second aperture defining a second inner diameter and a second inner surface;
wherein said second lens portion has a refractive index different from the refractive index of said first lens portion.

9. An intracorneal lens system according to claim 8, wherein
said first lens portion has a refractive index different from the refractive index of the cornea.

10. An intracorneal lens system according to claim 8, wherein
said second inner diameter is about one millimeter larger than said first outer diameter.

* * * * *